United States Patent [19]
Cohen et al.

[11] Patent Number: 5,880,134
[45] Date of Patent: Mar. 9, 1999

[54] METHOD FOR USING ERGOLINE COMPOUNDS TO EFFECT PHYSIOLOGICAL AND PATHOLOGICAL FUNCTIONS AT THE 5-HT$_7$ RECEPTOR

[75] Inventors: Marlene L Cohen, Carmel, Ind.; Daniel J Cushing, Phoenixville, Pa.

[73] Assignee: Eli Lilly and Company, Indianapolis, Ind.

[21] Appl. No.: 930,747
[22] PCT Filed: Mar. 20, 1996
[86] PCT No.: PCT/US96/03807
§ 371 Date: Oct. 7, 1997
§ 102(e) Date: Oct. 7, 1997
[87] PCT Pub. No.: WO96/32944
PCT Pub. Date: Oct. 24, 1996

[51] Int. Cl.$^6$ .................................................. A61K 31/44
[52] U.S. Cl. ............................................................. 514/288
[58] Field of Search ................................................ 514/288

[56] References Cited

U.S. PATENT DOCUMENTS

| | | |
|---|---|---|
| 4,714,704 | 12/1987 | Garbrecht et al. . |
| 4,931,447 | 6/1990 | Foreman et al. . |
| 4,981,859 | 1/1991 | Foreman et al. . |
| 4,999,355 | 3/1991 | Comte et al. . |
| 5,043,341 | 8/1991 | Cohen et al. . |
| 5,141,944 | 8/1992 | Cohen et al. . |

FOREIGN PATENT DOCUMENTS

| | | |
|---|---|---|
| 218433 | 4/1987 | European Pat. Off. . |
| 219257 | 4/1987 | European Pat. Off. . |
| 296748 | 12/1988 | European Pat. Off. . |
| 452074 | 10/1991 | European Pat. Off. . |
| 91/02527 | 3/1991 | WIPO . |
| 95/24200 | 9/1995 | WIPO . |

OTHER PUBLICATIONS

M.M. Foreman, et al., *The Journal of Pharmacology and Experimental Therapeutics,* vol. 260, No. 1, 1992, pp. 51–57.

Y. K. Gupta, et al., *Indian Journal of Pharmacology,* vol. 26, 1994, pp. 94–107.

R. G. Evans, et al., *Journal of Cardiovascular Pharmacology,* vol. 19, No. 6, 1992, pp. 1009–1017.

J. A. Bard, et al., *The Journal of Biological Chemistry,* vol. 31, pp. 23422–23426, 1993.

D. J. Cushing, et. al., *The Journal of Pharmacology and Experimental Theraputics,* vol. 261, pp.856–862, 1992.

D. J. Cushing, et al., *The Journal of Pharmacology and Experimental Therapeutics,* vol. 263, pp. 123–129, 1992.

T. W. Lovenberg, et al., *Neuron,* vol. 11, pp. 449–458, Sep. 1993.

P. Schumacher, et al., *European Journal of Pharmacology,* vol. 95, pp. 71–77, 1983.

Yong Shen, et al., *The Journal of Biological Chemistry,* vol. 24, pp. 18200–18204, 1993.

M. J. Sumner, et al., *British Journal of Pharmacology,* vol. 97, pp. 292–300, 1989.

Z. P. To, et al., *British Journal of Pharmacology,* vol. 15, pp. 107–116, 1995.

M. A. Trevethick, et al., *Life Sciences,* vol. 35, pp. 477–486, 1984.

J. M. Zgombick, et al., *Molecular Pharmacology,* vol. 40, pp. 1036–1042, 1991.

*Primary Examiner*—Raymond Henley, III
*Attorney, Agent, or Firm*—Robert D. Titus; David E. Boone

[57] ABSTRACT

The present invention provides a method for altering mammalian central and peripheral physiological and pathological functioning which is mediated by serotonin binding to the 5-HT$_7$ receptor. Specifically, the invention provides a method for antagonizing serotonin binding to the 5-HT$_7$ receptor.

14 Claims, 7 Drawing Sheets

METHOD FOR USING ERGOLINE COMPOUNDS TO EFFECT PHYSIOLOGICAL AND PATHOLOGICAL FUNCTIONS AT THE 5-HT$_7$ RECEPTOR

This application is a 371 of PCT/US96/03807 filed Mar. 20, 1996, published as WO96/32944 Oct. 24, 1996.

BACKGROUND

Serotonin mediated regulatory effects are pervasive throughout mammalian peripheral and central physiological functioning. These effects are mediated through binding of serotonin to multiple serotonin receptors at various locations in the mammalian body. Serotonin receptors in the mammalian body comprise different serotonin receptor subtypes. Serotonin binding to different receptor subtypes can cause different and often times inimical effects. Hence, in addition to the amount of serotonin released and the physiological/pathological status of a receptor, the clinical result of serotonin mediation is also affected by serotonin binding to more than one receptor subtype.

Presently, there are known to be at least 14 mammalian serotonin receptor subtypes. Recently researchers identified a novel serotonin receptor subtype designated as the "5-HT$_7$" receptor. mRNA for this receptor has been shown to exist in the mammalian central nervous system (CNS), kidney, vasculature, and various regions of the gastrointestinal tract. A homologous 5-HT$_7$ receptor has also been identified in the canine coronary artery. The presence of this unique receptor in the CNS and various peripheral smooth muscle tissues, provides the possibility for new therapeutic and diagnostic modalities through agonism and antagonism of the 5-HT$_7$ receptor.

Some compounds which bind to the 5-HT$_7$ receptor are well known in the art. In fact, binding studies of various known agonist and antagonist compounds were used to characterize the 5-HT$_7$ receptor. See Yong Shen et al., "Molecular Cloning and Expression of a 5-Hydroxytryptamine$_7$ Serotonin Receptor Subtype" *The J. of Biol. Chem.*, 264(24):18200–18204 (Aug. 24, 1993) [hereinafter "Shen"]; Timothy W. Lovenberg et al., "A Novel Adenylyl Cyclase-Activating Serotonin Receptor (5-HT$_7$) Implicated in the Regulation of Mammalian Circadian Rhythms", *Neuron*, 11:449–48 (Sept. 1993) [hereinafter "Lovenberg"]; Jonathan A. Bard et al., "Cloning of a Novel Human Serotonin Receptor (5-HT$_7$) Positively Linked to Adenylate Cyclase", *The J. of Biol. Chem.*, 268(31):23422–426 (Nov. 5, 1993) [hereinafter "Bard"]. Furthermore, the homology of the mammalian 5-HT$_7$ receptor was determined by comparison of the binding affinity of various known serotonin agonist and antagonist compounds to the 5-HT$_7$ receptor in the human, rat, and canine.

In addition to compounds which are known to bind to the 5-HT$_7$ receptor, the use of ergoline compounds to block non-5-HT$_7$ receptors is known in the art. However, ergoline compounds which provide selective high affinity binding to the 5-HT$_7$ receptor to cause the central and peripheral physiological effects disclosed herein have not been described previously.

SUMMARY OF THE INVENTION

Figure 1A:
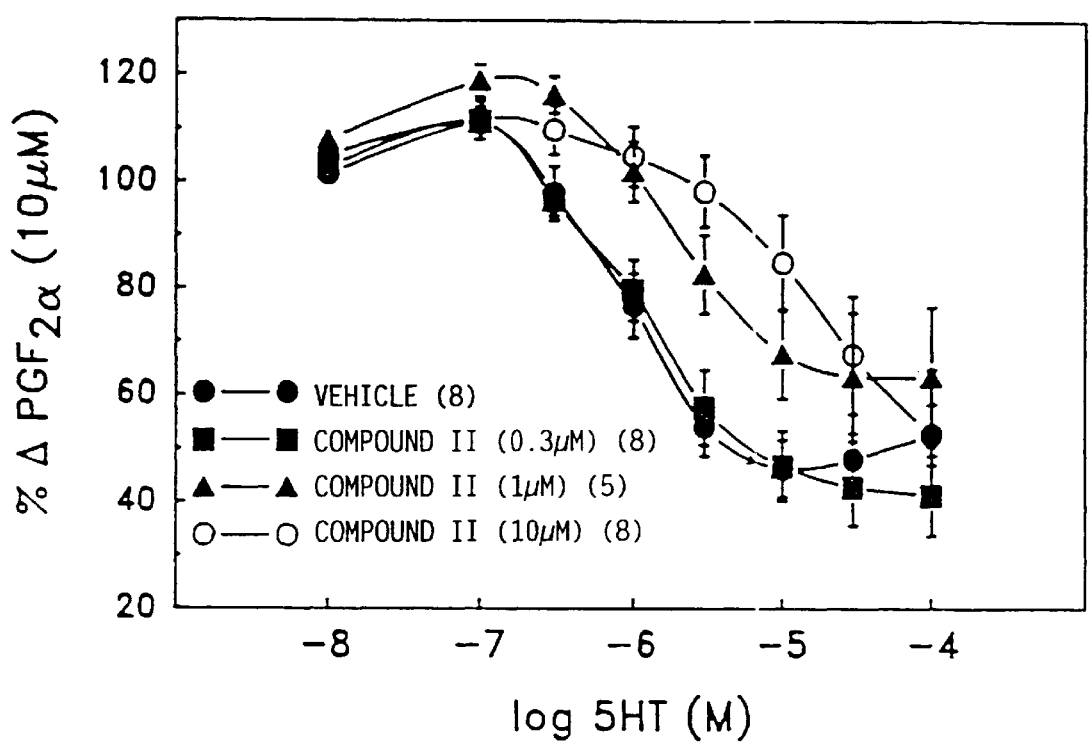
FIG. 1. (Upper panel) Concentration-relaxation response to 5-HT in the absence and presence of compound II (0.3–10 μM). (Lower panel) Schild plot for the data from the upper panel. The slope of the Schild regression was 0.92 and the pA$_2$ was 6.5.

The present invention provides a method for altering mammalian central and peripheral physiological and pathological functioning which is mediated by serotonin binding to the 5-HT$_7$ receptor. Specifically, the invention provides a method for antagonizing serotonin binding to the 5-HT$_7$ receptor.

In one embodiment, the invention provides a method for treating a mammal affected with a peripheral condition which is responsive to antagonism of a 5-HT$_7$ receptor. This includes conditions ameliorated by blocking smooth muscle relaxation caused by serotonin binding at peripheral 5-HT$_7$ receptors. The method comprises administering an effective amount of a 5-HT$_7$ antagonist compound having the general formula of:

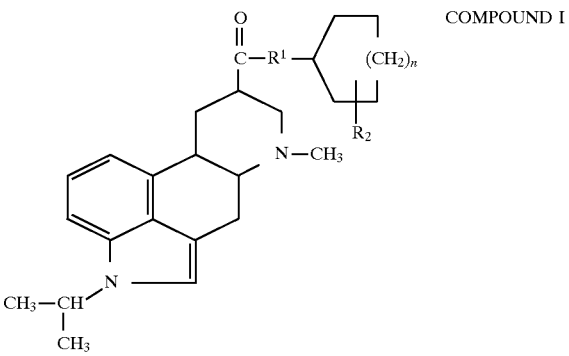

COMPOUND I wherein:
R$^1$=NH or O;
R$^2$=H or OR$^3$, wherein R$^3$ is a C$_1$–C$_6$ alkyl;
n=0 or 1; and
the pharmaceutically acceptable addition salts thereof.

Peripheral conditions ameliorated by inhibition of serotonin mediated smooth muscle relaxation include hypoperfusion conditions such as cardiovascular shock, septic shock, hypotension, hypovolemia and renal hypoperfusion (e.g., renal vascular spasm) and gastrointestinal conditions such as diarrhea, spastic colon, irritable bowel syndrome (IBS) and inflammatory bowel disease (IBD).

In another embodiment, the invention provides a method for treating a mammal affected with a central condition which is ameliorated by blocking serotonin binding at central 5-HT$_7$ receptors. The method comprises administering an effective amount of a 5-HT$_7$ antagonist compound having the general formula of compound I, or a pharmaceutically acceptable addition salt thereof. Central conditions amenable to treatment according to the method of the invention include circadian rhythm dysfunction, depression, schizophrenia, dementia, migraine headaches and sleep disorders.

Finally, the method of the invention provides a new and useful tool for further probing the role of serotonin in mammalian physiological and pathological functioning.

DETAILED DESCRIPTION OF THE INVENTION

The invention utilizes ergoline compounds as high affinity competitive antagonists which are selective for the 5-HT$_7$ receptor. The ergoline compounds useful according to the present invention are of the general formula:

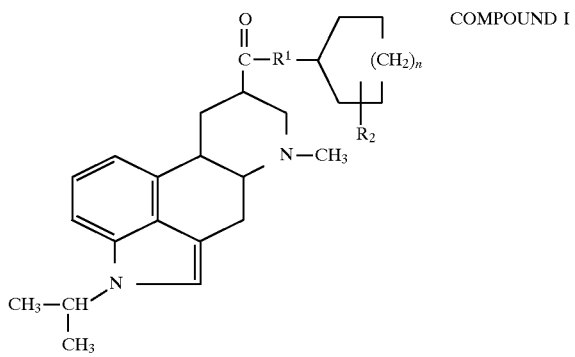

COMPOUND I wherein:
$R^1$-NH or O;
$R^2$=H or $OR^3$, wherein $R^3$ is a $C_1$–$C_6$ alkyl;
n=0 or 1; and
the pharmaceutically acceptable acid addition salts thereof.

As used herein the term "high affinity" means a binding affinity which is greater than 100 nM. According to the invention, binding affinity may be measured in terms of $K_D$, $K_i$, $K_B$, $-\log K_B$, $pA_2$ or other value used by those skilled in the art.

As used herein, the term "selective" means a compound having relatively slight affinity for adrenergic receptors such as $\alpha_1$, $\alpha_2$, $\beta$, histamine, carbachol and like receptors. The high affinity selective binding to the 5-HT$_7$ receptor, by the compounds employed by the invention, provide high potency antagonism of serotonin at the 5-HT$_7$ receptor as measured by blockade of relaxation of coronary artery responses to serotonin mediated by 5-HT$_7$ receptors.

As used herein, the term "condition" means any pathological or non-pathological syndrome, sign, symptom or physiological event from which a change is desired or beneficial to a mammal. The term "peripheral" refers to physiological or pathological conditions which are localized outside the central nervous system. The term "central" refers to physiological or pathological conditions which are localized to the central nervous system (CNS). And, while there is some debate by those of skill in the art as to the vascular versus neuronal origin of migraines and other headaches, for the purposes of the present disclosure such conditions are considered conditions of central origin.

In the present disclosure, guidance with respect to conditions amenable to treatment according to the method of the invention is provided in each instance by representative conditions. It is not meant, however, that the lists recited are exclusive.

Ergoline Compounds

Ergoline compounds employed by the present invention may be prepared by a variety of procedures well known to those of skill in the art. Methods for preparation of the compounds of the invention are disclosed in U.S. Pat. Nos. 4,714,704; 4,931,447; 4,981,859; 5,043,341 and 5,141,944 which are incorporated herein by reference. It is known in the relevant art that the compounds of the invention comprise one or more asymmetrical carbons. Accordingly, the method of the invention encompasses individual diastereoisomers and geometrical isomers as well as racemates of the disclosed compounds.

The invention also encompasses all pharmaceutically acceptable addition salts of the disclosed compounds. Pharmaceutically acceptable acid addition salts of the compounds of the invention include salts derived from inorganic acids such as hydrochloric acid, nitric acid, phosphoric acid, sulfuric acid, hydrobromic acid, hydriodic acid, phosphorous acid and similar inorganic acids. According to the invention, pharmaceutically acceptable acid addition salts also includes salts derived from organic acids such as aliphatic mono- and dicarboxylic acids, phenyl-substituted alkanoic acids, alkanedioic acids, aromatic acids, aliphatic and aromatic sulfonic acids, and similar organic acids. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1.4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, hippurate, lactobionate, methanesulfonate, propanesulfonate, naphthalene-1-sulfonate, naphthalene-2 sulfonate and like salts.

Preferred pharmaceutically acceptable acid additions salts are those formed with mineral acids such as hydrochloric acid.

The pharmaceutically acceptable acid addition salts of the compounds of this invention can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent. The hydrates are particularly useful, especially those of the hydrochloride salts.

The 5-HT$_7$ Receptor

Serotorin effects throughout the mammalian body are mediated through serotonin binding to serotonin receptors.

The ergoline compounds employed by the present invention are useful in the treatment of conditions responsive to inhibition of serotonin binding at 5-$HT_7$ receptors located throughout mammalian central and peripheral tissues. There are several known serotonin receptor subtypes. These receptors are generally referred to as "5-$HT_{(x)}$ receptors" wherein "x" is a number or a number and letter combination which is used to identify a specific serotonin receptor subtype. A central or peripheral physiological or pathological effect caused by serotonin receptor activation is dependent, in part, on which serotonin receptor subtype serotonin binds.

In the human, the 5-$HT_7$ receptor is found in multiple tissue locations. Using reverse transcription PCR techniques, high levels of 5-$HT_7$ mRNA was found in the brain, coronary artery and various regions of the gastrointestinal tract (including the stomach, descending colon, and ileum). Bard at 23425. High levels of 5-$HT_7$ receptors in the human coronary artery and gastrointestinal tract is consistent with the putative smooth muscle relaxant role of 5-$HT_7$ receptors. Bard at 23425.

The pharmacological profile of the human 5-$HT_7$ receptor as determined by competition of high affinity [$^3$H]5-HT binding is 5CT>5 MeOT≧5HT>8-OH DPAT wherein 5CT= 5-carboxamidotryptamine, 5 MeOT=5-methoxytryptamine, 5HT=5-hydroxytryptamine (serotonin) and 8-OH DPAT=8-hydroxy-2-(di-n-propyl-amino)-tetralin. Bard at 23423. A predominate characteristic of the 5-$HT_7$ receptor which is seen above, and is consistent with all mammalian 5-$HT_7$ pharmacological profiles studied, is the greater affinity of 5CT over serotonin for the 5-$HT_7$ receptor.

According to the method of the invention, it has been discovered that the compounds disclosed herein provide high affinity selective binding to the human 5-$HT_7$ receptor. High affinity binding to the human 5-$HT_7$ receptor was determined using receptor binding studies as described in J. M. Zgombick et al., "Expression and Pharmacological Characterization of a Canine 5-hydroxytryptamine$_{1D}$ Receptor Subtype" *Mol. Pharmacol.* 40:1036–1042 (1991). The general chemical structure for three particularly useful compounds of the invention (compounds III–V) are shown below:

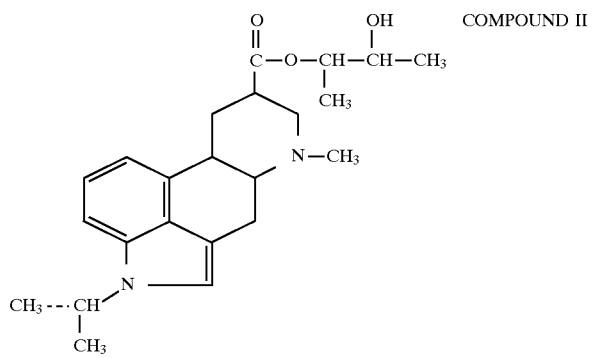

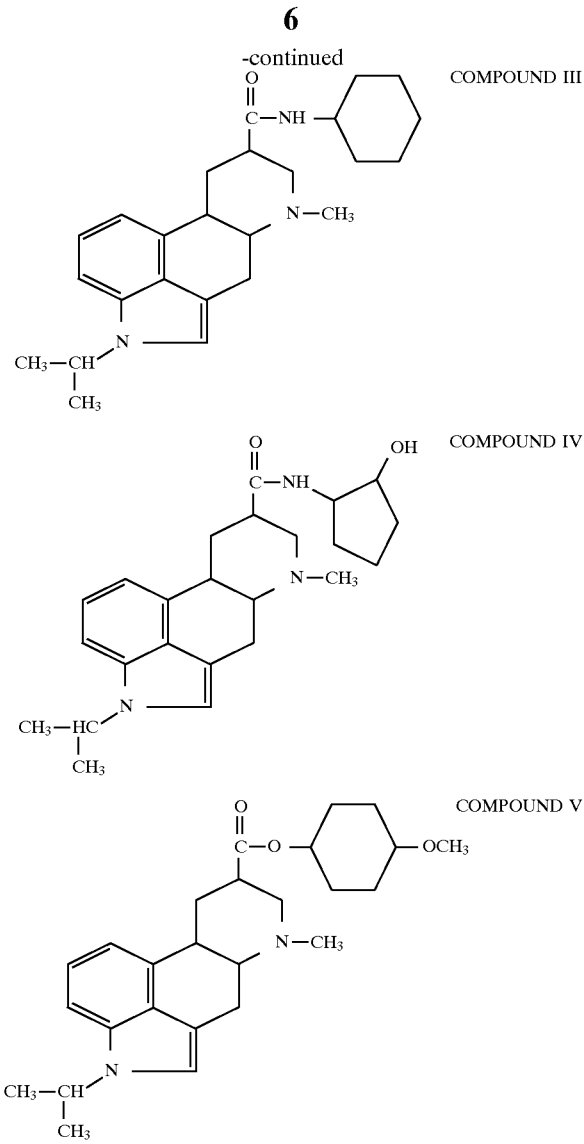

The $K_D$ and —log$K_B$ value for compound II, a known 5-$HT_7$ antagonist, and two compounds employed by the present invention, compound III and IV, are shown in Table 1.

TABLE 1

| Antagonist | $K_D$ (nM) | -log $K_D$ |
|---|---|---|
| COMPOUND II | 609 nM | 6.2 |
| COMPOUND III | 27.1 ± 1.5 nM | 7.6 |
| COMPOUND IV | 13.3 ± 1.2 nM | 7.9 |

As indicated in Table 1, antagonist compounds of the present invention (compounds III and IV) have a high binding affinity to the human 5-$HT_7$ receptor. The discovery of the high affinity binding of these compounds to the human 5-$HT_7$ receptor provides a new method for the treatment of human central and peripheral physiological and pathological conditions responsive to antagonism of serotonin at the 5-$HT_7$ receptor.

A known effect of serotonin activation of peripheral 5-$HT_7$ receptors is smooth muscle relaxation. Therefore, in one embodiment, the method of the invention provides for treating a human with a condition which is responsive to inhibition of serotonin mediated smooth muscle relaxation at the 5-HT$_7$ receptor. This includes, but is not limited to, vascular and gastrointestinal conditions. According to the invention, administration of an ergoline compound of the invention is useful for treating conditions ameliorated by inhibition of 5-HT$_7$ mediated vascular relaxation including systemic hypoperfusion conditions such as septic shock, cardiovascular shock, hypotension, hypovolemia and localized hypoperfusion conditions, for example, renal hypoperfusion (e.g., renal vascular spasm). Conditions ameliorated by inhibition of 5-HT$_7$ mediated gastrointestinal smooth muscle effects include, but are not limited to, gastrointestinal conditions such as diarrhea, spastic colon, IBS and IBD.

In another embodiment, the invention provides for treating a human affected with a condition responsive to antagonism of serotonin binding to central 5-HT$_7$ receptors which includes, but is not limited to, circadian rhythm dysfunction, depression, schizophrenia, dementia, headaches, including migraines, and sleep disorders.

The pharmacological profile and localization of the 5-HT$_7$ receptor found in human tissues is analogous to that found in the rat. The pharmacological profile of the rat 5-HT$_7$ receptor as determined by competitive binding studies of the nonselective 5-HT receptor antagonist lysergic acid diethylamide ([$^{125}$I]LSD) (Lovenberg at 451, Shen at 18202) and [$^3$H]5-HT (Shen at 18202) is 5CT>5MeOT≧5HT>8-OH-DPAT. Lovenberg at 451. Significant to the rat 5-HT$_7$ receptor system, and analogous to the human 5-HT$_7$ pharmacological profile, is the higher binding affinity of 5CT over serotonin. Moreover, like the human 5-HT$_7$ receptor, the rat 5-HT$_7$ receptor is positively coupled to adenylate cyclase. Bard at 23423, Lovenberg at 451, Shen at 18203.

The role of serotonin in behavioral and psychological functioning is well known. The effect of serotonin in resetting or causing phase shifts of circadian rhythms of neuronal activity in the suprachiasmatic nuclei (SCN) is also known in the art. Lovenberg at 449. In humans, disturbance of circadian rhythmicity causes mental fatigue and depression. Id. at 449. Because 5-HT$_7$ mRNA in the rat is located in the hypothalamus, particularly in neurons surrounding and possibly within the SCN, it is hypothesized that the 5-HT$_7$ receptor is responsible for the known serotonergic mediation of circadian rhythms. Lovenberg at 453. Accordingly, the inventors foresee the use of the compounds of the invention to inhibit serotonin mediated circadian rhythm phase advances. Hence, this provides a method for treating a human affected with, for example, jet lag and sleep disorders of a circadian nature.

The 5-HT$_7$ receptors blocked by the compounds employed by the present invention also play a role in psychiatric disorders. In addition to the 5-HT$_7$ receptor being located in various limbic and cortical regions of the brain, when expressed in mammalian cells, the 5-HT$_7$ receptor shows a high affinity to the antipsychotic drugs clozapine and loxapine, and the tricyclic antidepressant drug, amitriptyline. Shen at 18200. Therefore, the inventors foresee the use of the invention to treat psychiatric disorders which are responsive to blockade of serotonin at central 5-HT$_7$ receptors. This includes such conditions as depression, dementia and schizophrenia.

The homology of the human 5-HT$_7$ receptor and various functionally defined receptors in the blood vessels of non-human species is recognized in the art. Bard at 23422. The uniqueness of the canine coronary relaxant receptor among serotonin receptors described prior to characterization of the 5-HT$_7$ receptor has been discussed by various researchers including the inventors. Daniel J. Cushing et al. "Serotonin-Induced Relaxation in Canine Coronary Artery Smooth Muscle," *J. of Pharmacol Exptl. Ther.*, 263(1):123–129 (1992).

The Examples of the present invention provide specific detail for generation of pharmacological profiles which support the homology of the canine coronary artery relaxant receptor and the 5-HT$_7$ receptor. Like other members of the 5-HT$_7$ family of receptors the canine coronary artery relaxant receptor has a greater affinity for 5CT than for the endogenous agonist serotonin, a hallmark of the 5-HT$_7$ receptor.

The dissociation constants determined by antagonist effects in the canine coronary artery for the known 5-HT$_7$ antagonist, compound II, and three preferred compounds of the invention (compounds III–V) are shown in Table 2.

TABLE 2

| Antagonist | pA$_2$ (−log K$_B$) | (slope) |
|---|---|---|
| COMPOUND II | 6.5 | 0.92 |
| COMPOUND III | 6.7 | |
| COMPOUND IV | 8.3 | 0.98 |
| COMPOUND V | 6.4 | |

(One-way ANOVA; Tukey-Kramer; p < 0.05).

As discussed above, the 5-HT$_7$ receptor has been localized to the human coronary artery analogous to the canine coronary artery relaxant receptor. The following Examples provide functional studies which demonstrate the use of the invention to inhibit serotonin mediated vasodilation in tissue samples. Accordingly, the inventors foresee the use of the invention for treatment of conditions in mammals which are ameliorated by blockade of serotonin mediated vascular relaxation. Conditions which may be ameliorated according to the method of the invention include systemic hypoperfusion conditions, for example, septic shock, cardiovascular shock, hypotension, hypovolemia and localized hypoperfusion conditions such as renal hypoperfusion.

The discovery of the selective high affinity binding to the 5-HT$_7$ receptor by the compounds employed by this invention also provide a useful diagnostic modality for further understanding of the role of serotonin in mammalian physiological and pathological functioning. Moreover, discovery of compounds having selective high affinity binding to the 5-HT$_7$ receptor is fundamental to production of therapeutic agents of high therapeutic efficacy with minimal side effects.

EXAMPLES

Example 1

Tissue Preparation for Isolated Tissue Studies

Hearts were obtained from mongrel dogs anesthetized with sodium pentobarbital (30 mg/kg, i.v.) and placed in oxygenated modified Krebs' solution of the following composition (millimolar): NaCl, 118; KCl, 4.6; CaCl2, 1.6; KH$_2$PO$_4$, 1.2; MgSO$_4$ 1.2, glucose, 10; NaHCO$_3$ 24.8 (pH 7.4). The left anterior descending and circumflex coronary arteries were dissected from the hearts, cleaned of fat and adhering tissue and cut into rings (approximately 2–3 mm outer diameter and 4–5 mm in length). The intimal surface of the rings was gently rubbed with a pair of forceps to remove the endothelium. Tissues were then mounted between two stainless steel hooks and placed in 10 ml organ chambers constantly exposed to oxygenated modified Krebs' solution (95% O$_2$/5% CO$_2$; pH 7.4; 37° C.). Tissues were equilibrated for 1 hour under an initial optimal passive force of 4 g determined previously from length-tension experiments. The buffer was replaced every 15 minutes during equilibration. Isometric force was measured with Statham UC3 force transducers connected to a Beckman dynograph (R611). After 1 hr equilibration, tissues were depolarized twice with 50 mM KCl for 30 min with a 20 min washing period between. The integrity of the endothelium was examined with acetylcholine (1 μM), bradykinin (100 nM), or the ionophore A23187 (1 μM). Rings that relaxed to these agents were not used in this study.

Example 2

Experimental Protocol and Data Analyses

Tissues prepared as described in Example 1 were precontracted with $PGF_{2\alpha}$ (10 μM) which produced a tonic contraction that remained at or above 92.8±2.1% (n=14) of the original maximum force throughout the experiment. Cumulative concentration-response curves to 5-HT were generated in tissues incubated with either vehicle or antagonist for 1 hr. In some experiments contraction was measured in tissues under basal tone upon the cumulative addition of 5-HT. These tissues were treated with prazosin (1 μM) to block any potential a adrenoceptor activation and in the absence or presence of antagonist.

All results are expressed as mean ±S.E. where "n" represents the number of rings examined. No more than two rings were used from each animal for each compound studied. The relaxation data is expressed as percent relaxation of the contraction produced by $PGF_{2\alpha}$. The contraction data is expressed as percent of a maximal KCl (50 mM) contraction. The $EC_{50}$ was the concentration of the agonist producing half-maximal response and was determined by least squares linear regression analysis of the linear portion or the agonist concentration-response curve and expressed as $-\log C_{50}$ ($pEC_{50}$)

Apparent antagonist dissociation constants ($K_B$) were determined for each antagonist according to the following equation:

$$K_B = \frac{(B)}{(\text{dose ratio} - 1)}$$

where (B) is the concentration of the antagonist and dose ratio is the $EC_{50}$ of the agonist in the presence of the antagonist divided by the $EC_{50}$ of the agonist in vehicle treated tissues. These results were then expressed as the negative logarithm of the $K_B$ (i.e. $-\log K_B$). Significant differences between vehicle and antagonist treated tissues were determined with Student's t-test. The alpha value was set a priori at 0.05.

The data was also analyzed in accord with the procedure of Arunlakshana and Schild (1959). The dose ratio was determined at various concentrations of antagonist compound II or compound IV. If blockade is competitive under equilibrium conditions a plot of the logarithm (dose ratio—1) against the negative logarithm of the molar concentration of antagonist should yield a straight line whose slope is not different from unity and whose intercept on the abscissa is the $pA_2$, which is generally considered to be equivalent to $-\log K_B$.

Serotonin, acetylcholine, bradykinin, and A23187 were purchased from Sigma Chemical Co. (St. Louis, Mo.). compounds II–V were synthesized in the Lilly Research laboratories.

Example 3

Figure 1B:
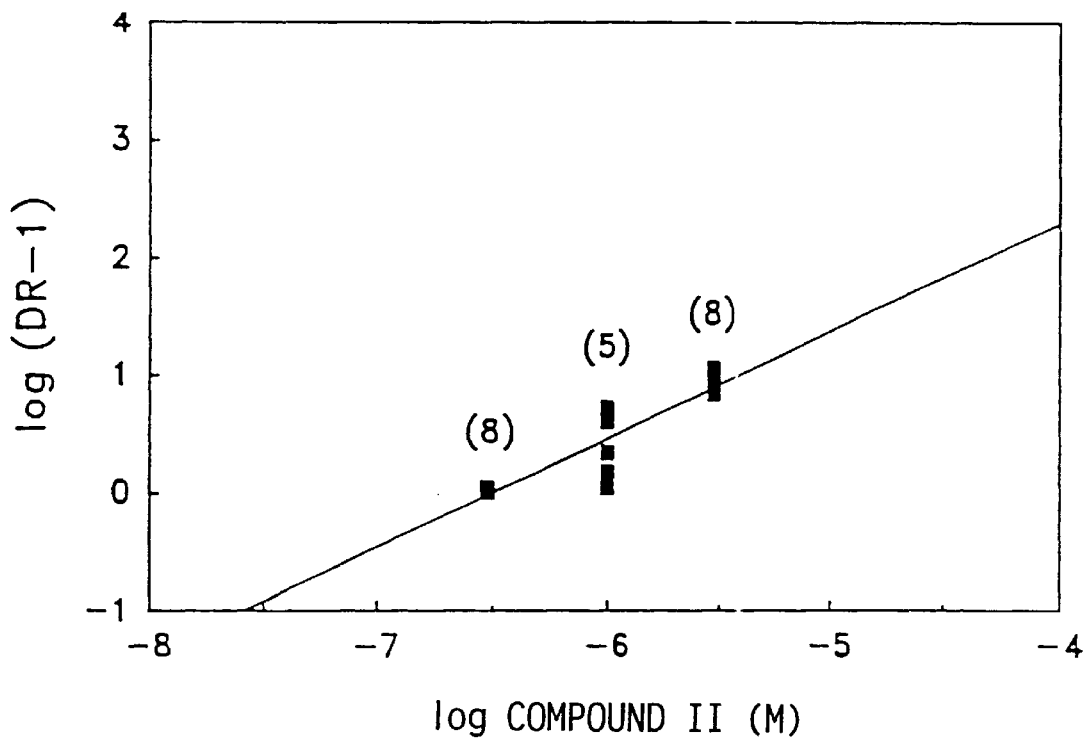

Effect of Ergoline Esters on 5HT-Induced Relaxation in Canine Coronary Vessels Contracted with $PGF_{2\alpha}$ In rings precontracted with $PGF_{2\alpha}$ (10 μM), compound II (0.3–10 μM) shifted the concentration-response curve to 5-HT significantly to the right and did not alter the maximum relaxant response (FIG. 1, upper panel). This antagonism was competitive as the slope of the Schild plot was not significantly different from unity (FIG. 1, lower panel). In addition, the $pA_2$ value for compound II was 6.5 (Table 2).

Figure 2:
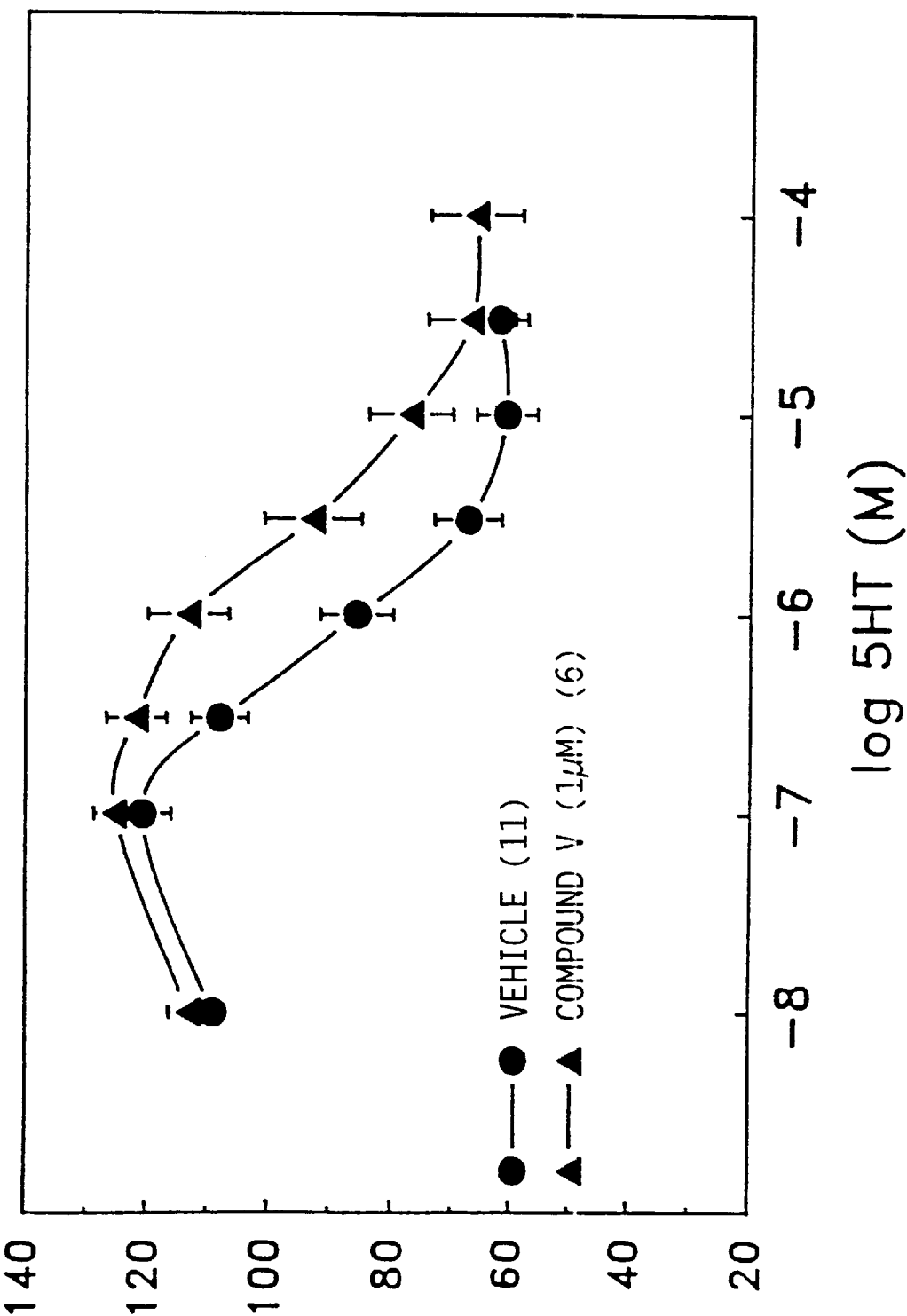
FIG. 2. Concentration-relaxation response to 5-HT in the absence and presence of compound V (1 μM).

In rats, after oral administration, compound V has a higher bioavailability than compound II. Compound V (1 μM), like compound II, blocked 5-HT-induced relaxation in an apparently competitive manner (FIG. 2). $pEC_{50}$ values between vehicle and compound V-treated tissues were significantly different (p<0.05; Student's t-test). In addition, the $-\log$ of the antagonist dissociation constant for compound V at the 5-$HT_7$ receptor in the dog coronary artery was 6.4 (Table 2).

Example 4

Figure 3:
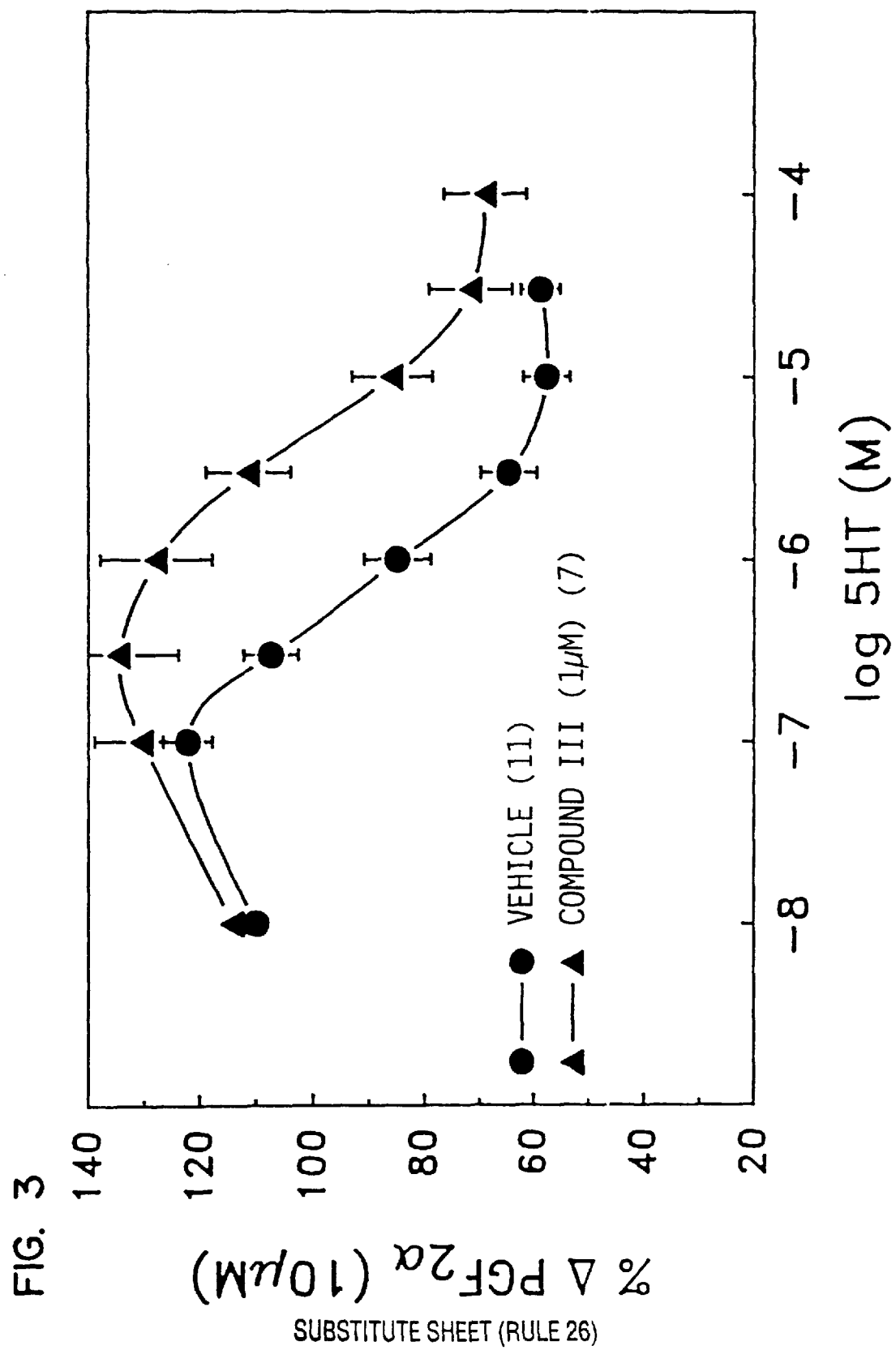
FIG. 3. Concentration-relaxation response to 5-HT in the absence and presence of compound III (1 μM).
Figure 4A:
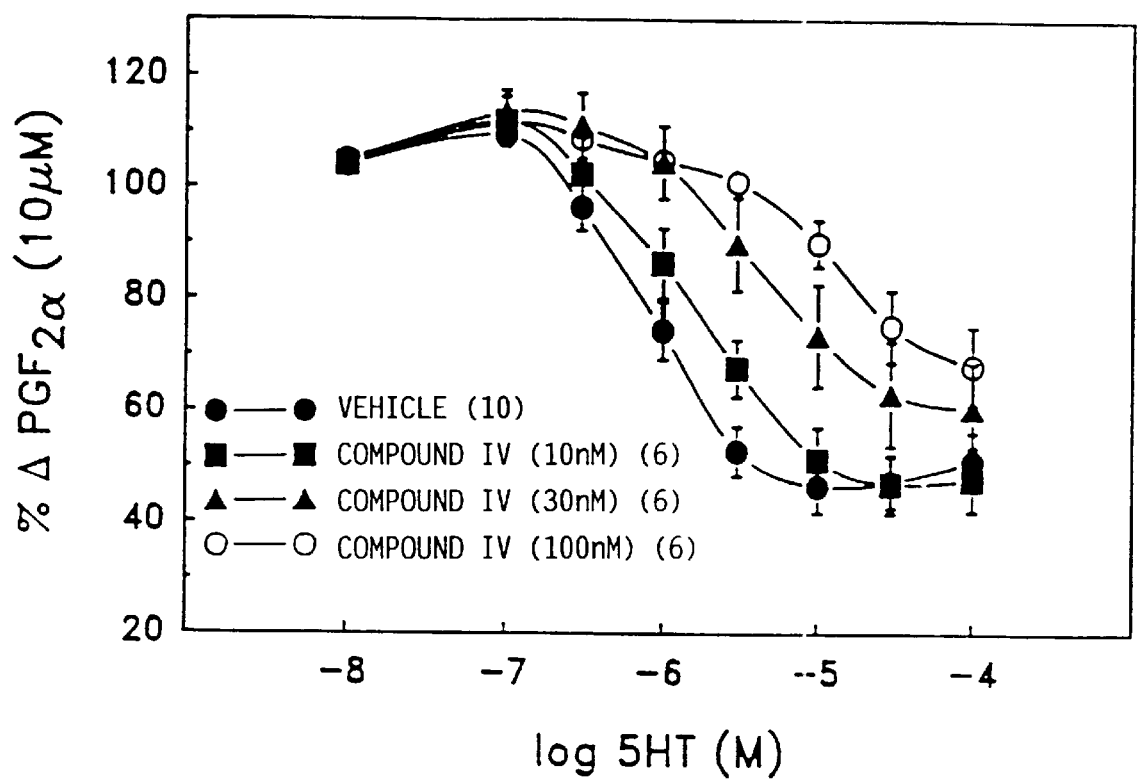
FIG. 4. (Upper panel) Concentration-relaxation response to 5-HT in the absence and presence of compound IV (10–100 nM). (Lower panel) Schild plot for the data from the upper panel.
Figure 4B:
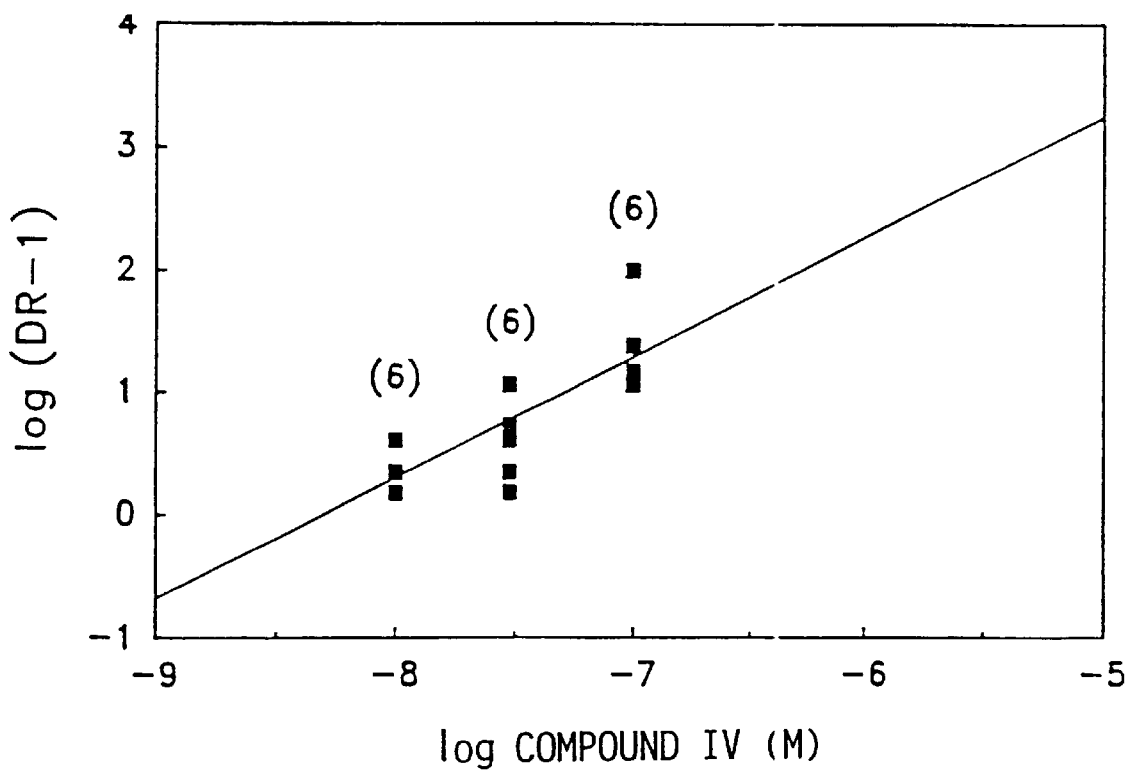

Effect of Ergoline Amides on 5-HT-induced Relaxation in Canine Coronary Vessels Contracted with $PGF_{2\alpha}$ In addition to examining the activity of the ergoline-esters at this receptor, the inventors examined the activity of two ergoline-amides at this site; compound III and compound IV. After oral administration in rats, compounds III and IV have a greater bioavailability than the ester compounds II and V. Compound III (1 μM) and compound IV (10–100 nM), blocked 5-HT-induced relaxation in endothelium-denuded canine coronary artery rings in a competitive manner (FIGS. 3, 4). The $-\log$ of the antagonist dissociation constant for compound III and compound IV was 6.7 and 8.3, respectively. In FIG. 3, $pEC_{50}$ values between vehicle and compound III-treated tissues were significantly different (p<0.05; Student's t-test). The slope of the Schild regression in the lower panel of FIG. 4 was 0.98 and the $pA_2$ was 8.3.

Example 5

Figure 5:
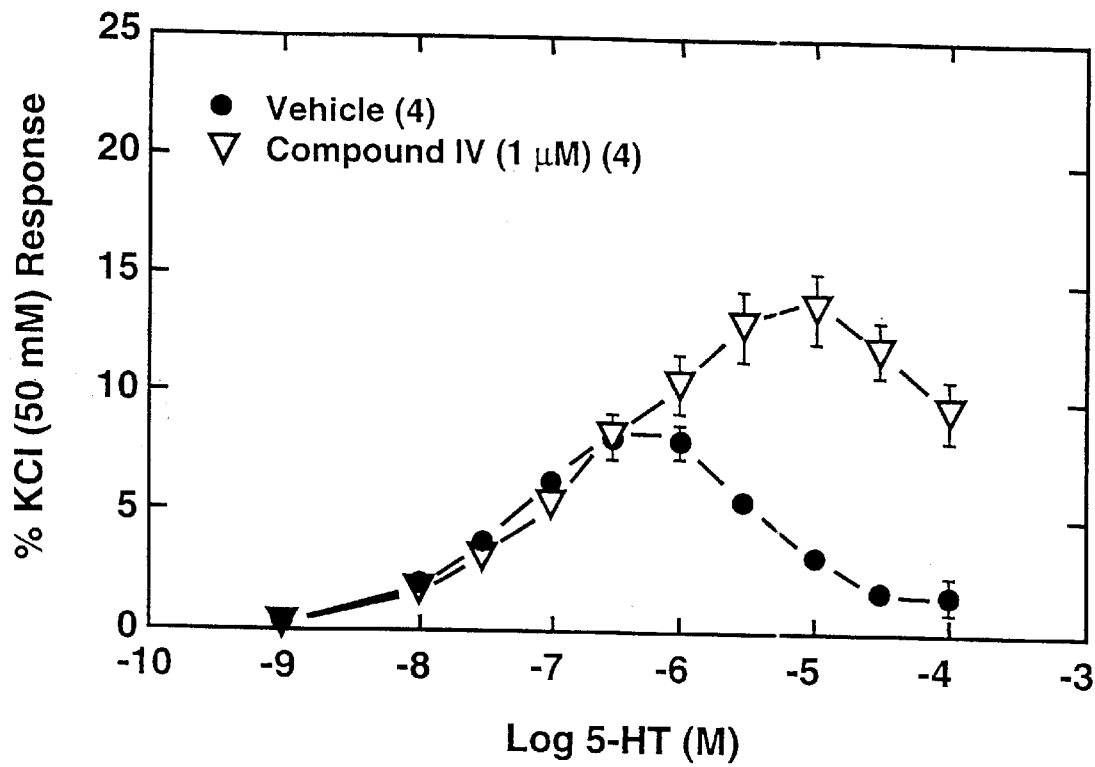
FIG. 5. (Upper panel) Concentration-response curve for 5-HT-induced contraction in endothelium denuded canine coronary artery under basal tone in the absence and presence of compound IV (1 μM). (Lower panel) Concentration-response curve for 5-MeOT-induced contraction in endothelium denuded canine coronary artery under basal tone in the absence and presence of compound IV (1 μM)
Figure 5:
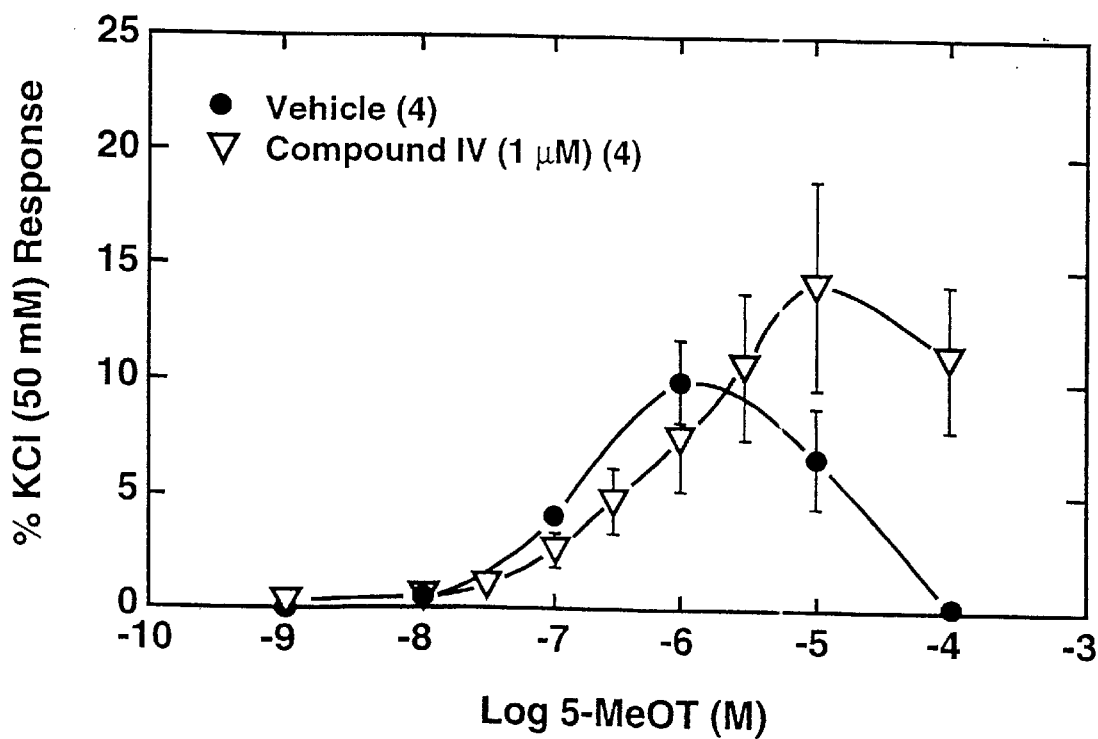

Effect of Compound IV on 5-HT-, 5-CT- and 5-MeOT-induced Contraction in Canine Coronary Vessels Under Basal Tone As previously reported in D. J. Cushing et al., "Comparison of the Serotonin Receptors that Mediate Smooth Muscle Contraction in Canine and Porcine Coronary Artery," *J. Pharmacol Exotl. Ther.* 856–862 (1992), along with their ability to dilate canine coronary artery, 5-HT and 5-MeOT produced a biphasic contractile response in vessels under basal tone (FIG. 5). Compound IV (1 μM) significantly attenuated the relaxant phase of this response while not affecting the contractile response produced by both agonists (FIG. 5).

Figure 6:
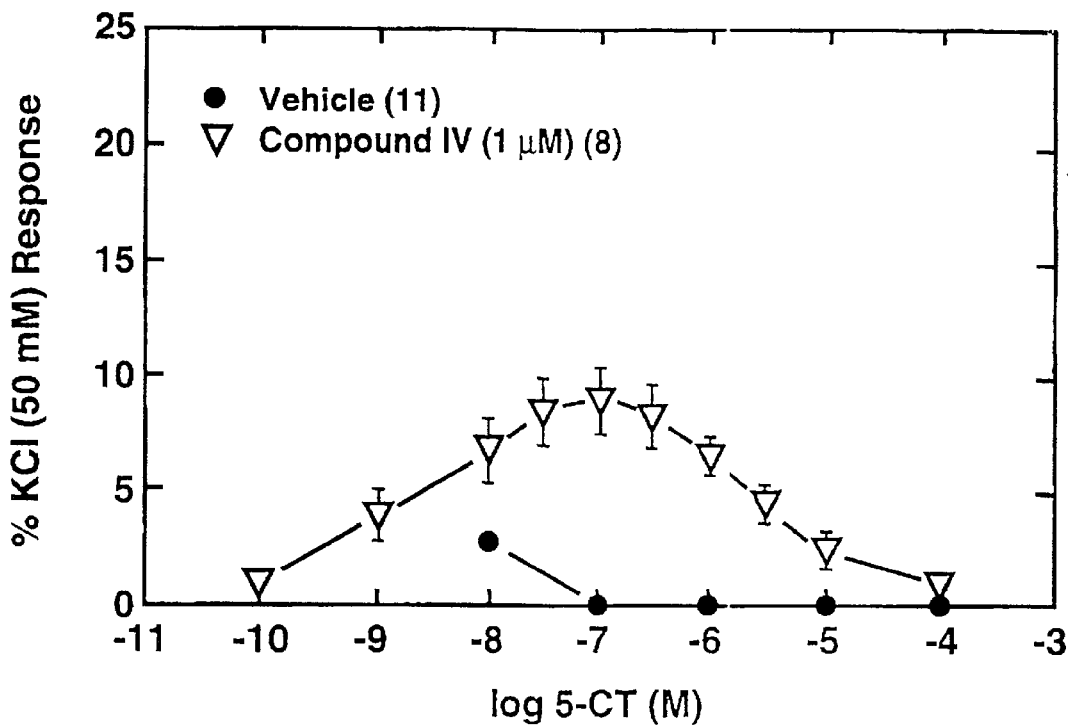
FIG. 6. (Upper panel) Concentration-response curve for 5-CT-induced contraction in endothelium denuded canine coronary artery under basal tone in the absence and presence of compound IV (1 μM). (Lower panel) Concentration-response curves for 5-CT-, 5-HT- and 5-MeOT-induced contraction endothelium denuded canine coronary artery under basal tone in the presence of compound IV (1 μM). Data are taken from FIG. 5 (upper and lower panels) and this figure's upper panel.
Figure 6:
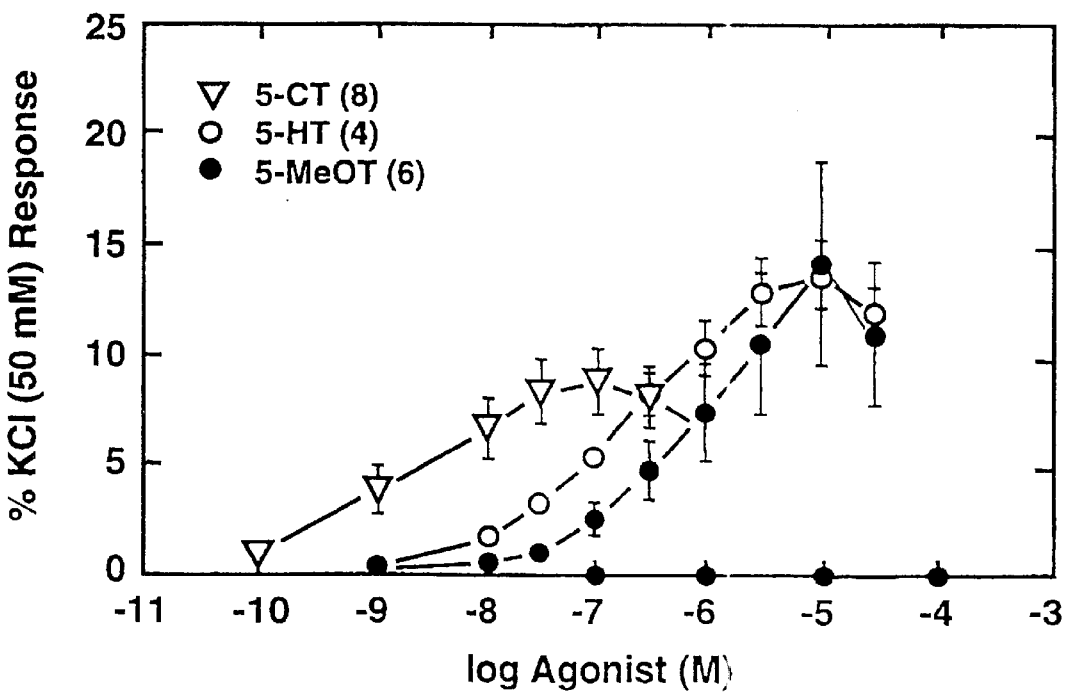
Figure 7:
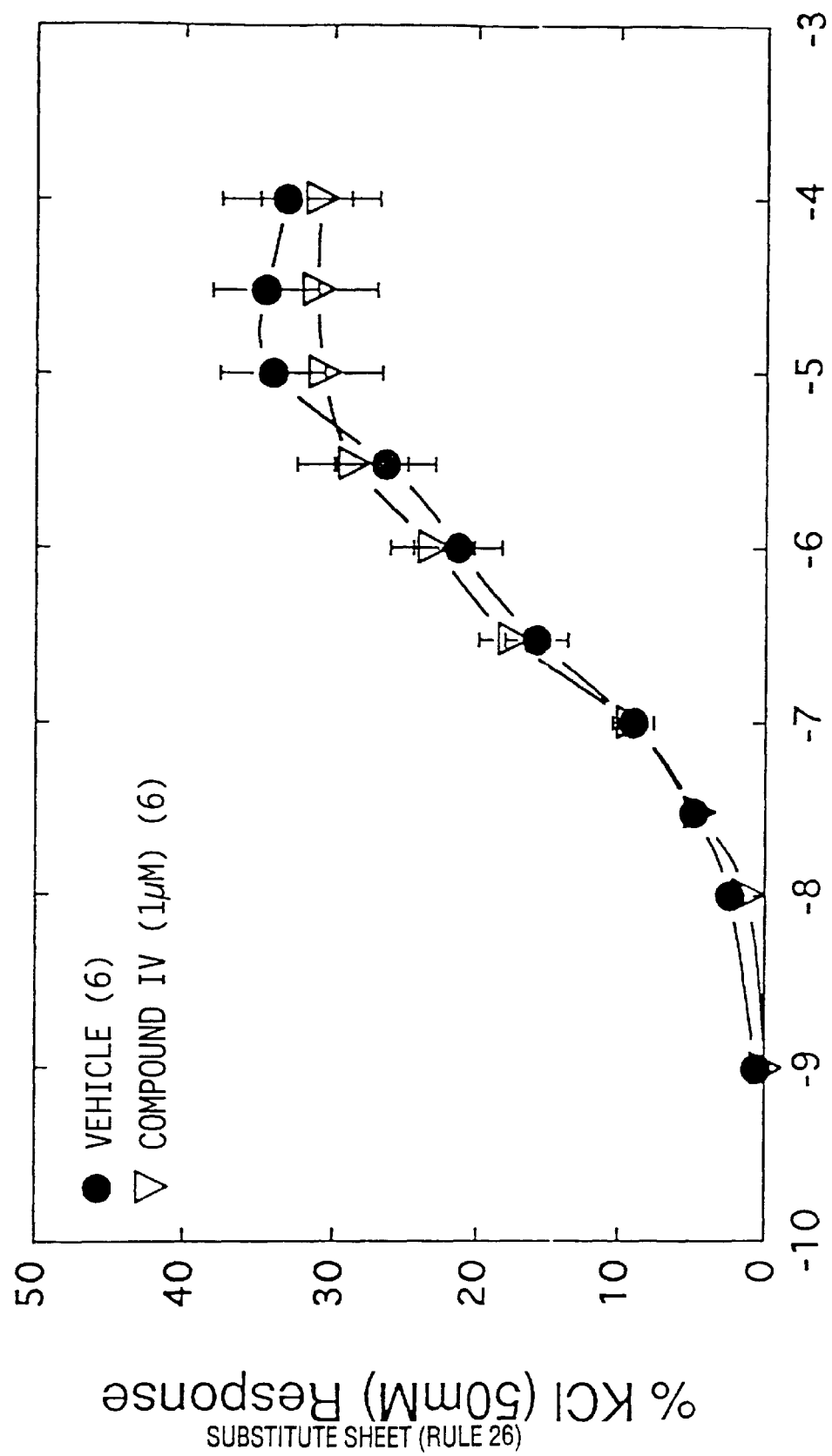
FIG. 7. Concentration-response curve for sumatriptan-induced contraction in endothelium denuded canine coronary artery under basal tone in the absence and presence of compound IV (1 μM).

5-CT did not significantly contract coronary arteries either under basal tone (FIG. 6, upper panel) or when precontracted; however, it was a potent relaxant agonist in canine coronary artery and has highest affinity for 5-$HT_7$ receptors. In the presence of compound IV (1 μM), to block 5-CT-induced relaxation, 5-CT concentration-dependently contracted canine coronary artery (FIG. 6, upper panel). To further document the selectivity of compound IV for the relaxant 5-HT receptor over the contractile 5-HT receptor in the canine coronary artery we examined the effect of compound IV (1 μM) on the contraction produced by sumatriptan, an agent lacking relaxant activity in this preparation. In confirmation of its selectivity, compound IV (1 μM) did not significantly affect sumatriptan-induced contraction (FIG. 7).

According to the method of the invention, a compound of the general formula of compound I is administered orally or parenterally to a mammal having a condition ameliorated by antagonism of serotonin binding at a peripheral or central 5-HT$_7$ receptor. The compounds of the present invention have previously been shown to have systemic effects after oral administration to rats.

For parenteral administration, a water soluble salt of the drug is dissolved in an isotonic salt solution, or other pharmaceutically acceptable carrier, and administered by the intravenous, intramuscular or subcutaneous route. For oral administration, a pharmaceutically-acceptable salt of the drug is mixed with standard pharmaceutical excipients such as starch and loaded into capsules or made into tablets, each containing 0.01 to 100 mg of active drug. Dosage levels of from about 0.01 to 30 mg/kg are effective in blocking 5-HT$_7$ receptors. Thus the oral dosage would be administered 1–4 times per day, giving a daily dosage range of about 0.01 to about 120 mg/kg per day.

The inventors further recognize that with time there may be discovery of additional physiological and pathological conditions mediated by serotonin binding to the 5-HT$_7$ receptor. Hence, in addition to the specific central and peripheral conditions which may be treated according to the method of the invention, the inventors foresee future therapeutic and diagnostic uses for the compounds of the invention in treatment of other effects mediated through the 5-HT$_7$ receptor.

All publications and patents in this specification are indicative of the level of ordinary skill in the art to which this invention pertains. All publications and patents are herein incorporated by reference to the same extent as if each individual publication or patent application was specifically and individually indicated by reference.

It will be apparent to one of ordinary skill in the art that many changes and modifications can be made in the invention without departing from the spirit or scope of the appended claims.

We claim:

1. A method of inhibiting the 5-HT$_7$ receptor in a mammal, comprising administering to a mammal in need of such inhibition a 5-HT$_7$ inhibiting dose of a compound of formula

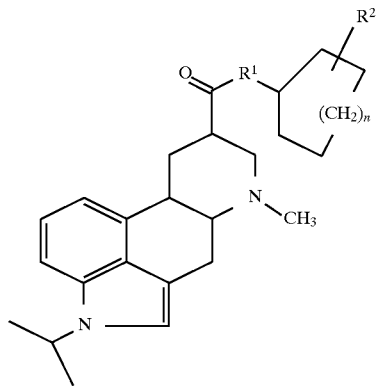

wherein:

R=NH or O;

R$^2$=H or OR$^3$ wherein R$^3$ is a C$_1$–C$_6$ alkyl;

n is 0 or 1; or a pharmaceutically acceptable salt thereof.

2. A method of claim 1 where the mammal is suffering from cardiovascular shock.

3. A method of claim 1 where the mammal is suffering from septic shock.

4. A method of claim 1 where the mammal is suffering from hypotension.

5. A method of claim 1 where the mammal is suffering from hypovolemia.

6. A method of claim 1 where the mammal is suffering from renal hypoperfusion.

7. A method of claim 1 where the mammal is a human.

8. A method of inhibiting the 5-HT$_7$ receptor in a mammal, comprising administering to a mammal in need of such inhibition a 5-HT$_7$ inhibiting dose of a compound of formula

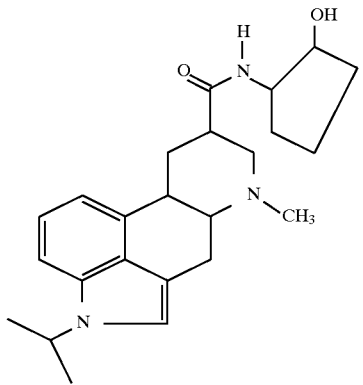

or a pharmaceutically acceptable salt thereof.

9. A method of claim 8 where the mammal is suffering from cardiovascular shock.

10. A method of claim 8 where the mammal is suffering from septic shock.

11. A method of claim 8 where the mammal is suffering from hypotension.

12. A method of claim 8 where the mammal is suffering from hypovolemia.

13. A method of claim 8 where the mammal is suffering from renal hypoperfusion.

14. A method of claim 8 where the mammal is a human.

* * * * *